United States Patent [19]

Janakiram et al.

[11] Patent Number: 6,143,303
[45] Date of Patent: Nov. 7, 2000

[54] ANALGESIC ANTI-INFLAMMATORY COMPOSITION AND METHOD OF PREPARING FROM DODONAEA SP

[76] Inventors: Chodavarapu Janakiram, C.I.J.R. Technical Consultancy Services and Research Foundation, 805 Asisa House, K/G. Marg, New Delhi 110 001, India; Mahmud Khalilullah, C.I.J.R. Technical Consultacy Services and Research Foundation, 805 Asisa House, K/G. Marg, New Delhi 110 001, India

[21] Appl. No.: 09/374,834

[22] Filed: Aug. 14, 1999

[51] Int. Cl.$^7$ ...................................................... A61K 7/40
[52] U.S. Cl. ........................ 424/195.1; 424/404; 424/405; 424/455
[58] Field of Search ................................. 424/195.1, 404, 424/405, 455

[56] References Cited

U.S. PATENT DOCUMENTS 3,787,499  1/1974  Grant .
3,797,494  3/1974  Zaffaroni ................................. 128/268
5,155,276  10/1992  Paul .
5,425,885  6/1995  Zhao .
5,639,460  6/1997  Raymond .

OTHER PUBLICATIONS

Hoffman, D. The Herbal Handbook; pp. 209–211, 1987.
Wagner et al. Biologically Active Saponins from Dodonaea Viscosa: Phytochemistry, vol. 26, No. 3, pp. 697–701, 1987.
Ghisalberti et al. Ethnopharmacology and Phytochemistry of *Dodonaea Species*: No. 2 pp. 99–11, 1987.

*Primary Examiner*—Jon P. Weber
*Assistant Examiner*—Patricia Patten
*Attorney, Agent, or Firm*—Michael I. Knoll

[57] ABSTRACT

An anti-inflammatory, analgesic composition is prepared using an extract from a plant of the family Dodonaea in a dermatologically acceptable carrier, with or without a dermal absorption enhancer such as eucalyptus oil. The extract is prepared by solvent extraction of the plant matter, either whole or separated into various parts, such as leaves, bark, seeds, roots and flowers.

5 Claims, 1 Drawing Sheet

ANALGESIC ANTI-INFLAMMATORY COMPOSITION AND METHOD OF PREPARING FROM DODONAEA SP

BACKGROUND OF THE INVENTION

1. Field of the Invention

The instant invention relates generally to topically-applied pharmaceutical compositions for providing analgesic and anti-inflammatory relief in humans and more specifically to compositions containing an extract of the Hop Bush plant (Dodonaea sp.). The invention also relates to a process for preparing such a therapeutic extract from the raw plant material of the Hop Bush plant.

2. Description of the Prior Art

Topical compositions for providing pain relief and anti-inflammatory action are known in the art, For example, U.S. Pat. No. 5,178,879 (Adekunle, M. et al., Jan. 12, 1993) discloses a topical pain relief gel containing capsaicin, water, alcohol and a carboxypolymethylene emulsifier.

U.S. Pat. No. 5,288,491 (Moniz, H., Feb. 22, 1994) discloses a method for processing the noni (*Morinda citrifolia*) plant into powder for use in therapeutic compositions.

U.S. Pat. No. 5,560,910 (Crandall, W. T., Oct. 1, 1996) discloses a topical anti-inflammatory composition containing bromelain, capsaicin and a penetrating agent selected from n-decylmethyl sulfoxide and lecithin organogel.

BRIEF SUMMARY OF THE INVENTION

The present invention is concerned with a topical composition for providing analgesic and anti-inflammatory relief in humans and more specifically to a composition containing an extract of the Hop Bush plant (Dodonaea sp.). The inventive extracts and compositions including such extracts have potent analgesic and anti-inflammatory properties and are thus useful in the treatment of conditions involving pain and/or inflammation, such as, for example, migraines, musculoskeletal and joint disorders, and the like.

A primary object of the present invention is to provide a topical analgesic and anti-inflammatory composition containing a therapeutic amount of a compound extracted from the Hop Bush plant.

Another object of the present invention is to provide a topical analgesic and anti-inflammatory composition containing a compound extracted from the Hop Bush plant in conjunction with a dermal absorption enhancer such eucalyptol or eucalyptus oil.

An additional object of the present invention is to provide a substantially pure compound derived from the Hop Bush plant which is effective both as an analgesic and as an anti-inflammatory in human subjects.

Another object of the present invention is to provide a process for preparing an extract from the Hop Bush plant for use in a topical therapeutic composition.

A further object of the present invention is to provide a process for preparing a substantially pure therapeutic compound from the Hop Bush plant for use in a topical therapeutic composition.

Another object of the present invention is to provide a topical therapeutic composition having little or no side effects.

A further object of the present invention is to provide a topical therapeutic composition which is economical in cost to manufacture.

Yet another object of the present invention is to provide a topical therapeutic composition which can be prepared in the form of a gel, lotion, ointment, spray, liquid and the like.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 graphically depicts a plant characterized as *Dodonaea petiolaris* herein.

DETAILED DESCRIPTION OF THE PREFERRED EMBODIMENTS

Figure 1:

The present invention relates to the use of a plant from the genus Dodonaea in the manufacture of therapeutic compositions for use in mammals, including humans in need of such therapeutic treatment.

The hop bush plant generically refers to the plant genus Dodonaea, a fairly large group of tender trees and shrubs mainly of Australian origin, although several species are found in New Zealand, North America, Africa and Hawaii. Exemplary species include *Dodonaea cuenta*, also known as the wedge leaf hop bush, *Dodonaea viscosa*, known as the giant hop bush, *Dodonaea viscosa purpurea*, the purple ake-ake of New Zealand, and *Dodonaea petiolaris*, known as "Giant Lanterns" and grown widely in the southern regions of India. All members of the genus Dodonaea examined have exhibited some degree of bioactivity, and are within the scope of the present invention.

While many of the various varieties of the hop bush plant are cultivated for ornamental and agricultural uses, the present inventors are the first to recognize the pharmaceutical utilities for the plant, particularly with regard to the production of concentrated plant extracts having biological activity.

The present invention concerns the processing of the raw plant material in order to obtain the therapeutic components of the plant in a concentrated form, or extract, which can be incorporated into therapeutic compositions for use by human patients. The term "extract," as used herein, refers to any form of processed, concentrated plant matter, including, for example, resins, oils, powders, absolutes, concretes, and purified compounds and mixtures thereof in any form. Any process which concentrates the therapeutic components of the raw plant is within the scope of the present invention.

As discussed above, all members of the plant genus Dodonaea find utility in practicing the present invention.

Examples include, without limitation, *Dodonaea petiolaris, Dodonaea viscosa, Dodonaea adenophora, Dodonaea boroniifolia, Dodonaea oxyptera, Dodonaea ptarmicaefolia* and *Dodonaea triquetra*. In the following section, *Dodonaea petiolaris* and *Dodonaea viscosa* were utilized interchangeably, with both species exhibiting excellent therapeutic activity. It is expected that all species of the genus Dodonaea will exhibit similar activity.

With regard to the processing of the raw plant material, it has been determined that active components are not localized to any one region of the plant. Portions of the plant from which active components have been extracted include, for example, the roots, leaves, bark, flowers and seeds. In practicing the invention, the entire plant can be utilized, or alternatively, different portions of the plant can be removed and then utilized individually or collectively. The following examples illustrate extraction methods for various regions of the plant.

Speaking generally, the raw plant material will be processed accordingly to standard practice. The preferred processing method is solvent extraction. A wide variety of solvents may be used as is well known in the art. Suitable solvents include, for example, n-hexane, petroleum ether, ethylacetate, acetone, ethanol (typically 95%), diethyl ether, benzene and toluene, although any conventional extraction solvent may be suitably employed. A preferred solvent extraction method incorporates a series of successive extractions in the same or different solvents, with the choice of solvent depending on several factors such as availability, cost, plant species, the portion of the plant being extracted, and the like. For example, the aerial parts (flowers and seeds) may be suitable extracted with benzene, n-hexane and petroleum ether; the leaves with ethanol, diethyl ether and petroleum ether.

Prior to extraction, the raw plant material can preferably be processed to increase the surface area in order to improve the efficiency of the extraction process. The most preferred pre-extraction processing includes one or more of: 1) separating the plant regions (e.g., roots, leaves, seeds, flowers, bark, etc.); 2) drying the plant material; and 3) chopping, shredding, crushing, grinding, mashing or otherwise pulverizing the plant material, for example, into a fine or coarse powder.

EXAMPLES

Example 1 Solvent Extraction of the Roots

The roots of *Dodonaea petiolaris* and *Dodonaea viscosa* were removed from the plant, dried and then ground into powder. The powdered roots were then extracted successively by conventional methods with a series of organic solvents (n-hexane, petroleum ether, ethylacetate, acetone, (95%) ethanol, diethyl ether, benzene and toluene). The organic solvents were recovered by distillation and the residues thus obtained were mixed and termed as an absolute for incorporation into the compositions of the present invention.

Example 2 Solvent Extraction of the Bark

The bark of *Dodonaea petiolaris* and *Dodonaea viscosa* was removed from the plant, dried and then ground into a coarse powder. The powdered bark was then extracted successively by conventional methods with a series of organic solvents (n-hexane, petroleum ether, ethylacetate, acetone, (95%) ethanol, diethyl ether, benzene and toluene). The organic solvents were recovered by distillation and the residues thus obtained were mixed and termed as an absolute for incorporation into the compositions of the present invention or for recombination with the absolute obtained from Example 1.

Example 3 Solvent Extraction of the Leaves

The leaves of *Dodonaea petiolaris* and *Dodonaea viscosa* were removed from the plant, dried and then ground into powder. The powdered roots were then extracted successively by conventional methods with a series of organic solvents (n-hexane, petroleum ether, ethylacetate, acetone, (95%) ethanol, diethyl ether, benzene and toluene) at their respective boiling points. The organic solvents were recovered by distillation. Traces of solvents were removed under mild vacuum. An oily residue was thus obtained for incorporation into the compositions of the present invention or for recombination with the absolute obtained from Example 1 or the recombination obtained from Example 2.

Example 4 Solvent Extraction of the Seeds

The seeds of *Dodonaea petiolaris* and *Dodonaea viscosa* were picked during the months from October to January in India. The seeds were dried and then crushed. The powdered seeds were then extracted successively by conventional methods with a series of organic solvents (n-hexane, petroleum ether, ethylacetate, acetone, (95%) ethanol, diethyl ether, benzene and toluene). The organic solvents were recovered by distillation. Traces of solvents were removed under mild vacuum. A yellow, oily residue was thus obtained for incorporation into the compositions of the present invention or for recombination with the absolute obtained from Example 1 or the recombinations obtained from Examples 2 and 3.

Example 5

As described in Examples 1 through 4, above, an extract was prepared via solvent extraction of the separated leaves, roots, bark and seeds of *Dodonaea petiolaris* and *Dodonaea viscosa*, followed by recombination of the four extracts thus obtained. This recombined residue was again subjected to solvent extraction with 95% ethanol. The solvent was recovered by distillation and traces of the solvent were removed under mild vacuum, yielding a concentrated absolute. The absolute thus obtained can then be subjected to oxidation under conditions which both include and exclude an oxidizing agent.

Example 6

The absolute obtained in Example 5 was oxidized by exposure to gaseous oxygen for about 20 hours at an ambient temperature of about 35 to 40° C.

Example 7

The absolute obtained in Example 5 was oxidized by exposure to a free current of air at ambient temperature (about 35 to 40° C.) for about 744 hours with continuous stirring.

Example 8

The absolute obtained in Example 5 was oxidized by exposure to a free current of air at a temperature of about 85 to 90° C. for about 72 hours with continuous stirring.

The product of each of the examples above exhibited significant therapeutic activity in mammalian subjects. The extracts thus prepared can be used directly or incorporated into therapeutic compositions for topical use, for example, ointments, lotions, liniments, liquid preparations, sprays, and the like. The compositions of the invention exhibit powerful anti-inflammatory and analgesic activity and thus find great utility in treating conditions involving pain and/or inflammation. Furthermore, the compositions of the invention act rapidly, often providing relief (i.e., 80 to 90% reduction in pain) within 10 to 15 minutes of application, in addition to being effective for up to 24 hours with no observed side-effects. Accordingly, the compositions of the invention find great utility in treating conditions and disorders such as, for example, low back pain, arthritis, osteoarthritis; rheumatoid arthritis, gout, spondylosis, cramps, headaches, joint pain, lumbago, migraines, muscle pain, acute and chronic musculoskeletal disorders, nerve disorders, rheumatism, sciatica, sprains, strains, snake/spider bites, toothaches and the like.

The anti-inflammatory, analgesic composition of the present invention comprises an extract from a plant of the family Dodonaea in a dermatologically acceptable carrier such as petroleum jelly, vegetable oil, grapeseed oil, animal oil, mineral oil, trichlorofluoromethane, dichlorodifluoromethane, Allium sativum, Cinnamimum camphora and Ricinus communis.

It will be understood that each of the elements described above, or two or more together, may also find a useful application in other types of applications differing from the type described above. These include, for example, cardiac care, myocardial infarction, transient ischemic attacks, strokes, blood clots, colorectal cancer, migraines, cataracts, immunity, Alzheimer's disease, arthritis, fever, pain, inflammation, pre-eclampsia and eclampsia.

While the invention has been illustrated and described as embodied in a therapeutic composition and method of preparing same, it is not intended to be limited to the details shown, since it will be understood that various omissions, modifications, substitutions and changes in the forms and details of the formulation illustrated and in its operation can be made by those skilled in the art without departing in any way from the spirit and scope of the present invention. For example, any conventional extracting solvent or combination of extracting solvents may be utilized instead of the specific combination and order of solvents described. Also, any species of the genus Dodonaea may be used, rather than the *Dodonaea petiolaris* and *Dodonaea viscosa* described. And although individual extractions for each part of the plant have been described, it should be appreciated that the plant can be processed whole instead.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

We claim:

1. A process for preparing a biologically active component from the plants *Dodonaea petiolaris* and *Dodonaea viscosa* comprising the steps of:
    a) separating the plant matter into groups, said groups including roots, leaves, bark, seeds and flowers;
    b) preparing individual extracts of said roots, leaves, bark, seeds and flowers by organic solvent extractions;
    c) combining the extracts obtained from each of said roots, leaves, bark, seeds and flowers into a residue;
    d) subjecting said residue to solvent extraction with ethanol;
    e) recovering the solvent by distillation and removing traces of the solvent under mild vacuum yielding a concentrated absolute; and
    f) oxidizing said absolute by exposure to gaseous oxygen for about 20 hours at an ambient temperature of about 35 to 40 deg. C.

2. The method of claim 1 in which said oxidizing is conducted by exposing said absolute to a free current of air at ambient temperature for about 744 hours with continuous stirring.

3. The method of claim 1 in which said oxidizing is conducted by exposing said absolute to a free current of air at a temperature of about 85 to 90 deg. C. for about 72 hours with continuous stirring.

4. The anti-inflammatory, analgesic composition obtained from the method described in claim 1.

5. A method of treating an inflammatory condition in a patient comprising the step of topically administering to a patient in need of such treatment the anti-inflammatory, analgesic composition recited in claim 4 in a dermatologically acceptable carrier and a dermal absorption enhancer.

* * * * *